(12) United States Patent
Sugai et al.

(10) Patent No.: US 8,440,645 B2
(45) Date of Patent: May 14, 2013

(54) CERAMIDE PRODUCTION PROMOTER

(75) Inventors: Yoshiya Sugai, Haga-gun (JP); Hiroshi Hashimoto, Haga-gun (JP); Shinya Amano, Haga-gun (JP); Shotaro Ito, Haga-gun (JP); Yoshie Shimotoyodome, Haga-gun (JP); Yoriko Nakagiri, Haga-gun (JP)

(73) Assignee: Kao Corporation, Tokyo (JP)

( * ) Notice: Subject to any disclaimer, the term of this patent is extended or adjusted under 35 U.S.C. 154(b) by 82 days.

(21) Appl. No.: 13/001,701

(22) PCT Filed: Jul. 30, 2009

(86) PCT No.: PCT/JP2009/003605
§ 371 (c)(1),
(2), (4) Date: Dec. 28, 2010

(87) PCT Pub. No.: WO2010/013474
PCT Pub. Date: Feb. 4, 2010

(65) Prior Publication Data
US 2011/0105439 A1 May 5, 2011

(30) Foreign Application Priority Data

Jul. 31, 2008 (JP) ................. 2008-197958
Jul. 31, 2008 (JP) ................. 2008-197959

(51) Int. Cl.
*A61K 8/55* (2006.01)
*A61Q 19/00* (2006.01)
*C07F 9/06* (2006.01)

(52) U.S. Cl.
USPC ................ 514/120; 514/129; 562/23; 562/24

(58) Field of Classification Search .................. None
See application file for complete search history.

(56) References Cited

U.S. PATENT DOCUMENTS

| 4,734,225 | A | * | 3/1988 | Eibl ............................. 552/105 |
| 5,238,965 | A | | 8/1993 | Piazza et al. |
| 5,723,136 | A | | 3/1998 | Tanaka et al. |
| 2004/0009140 | A1 | | 1/2004 | Nishijima et al. |

FOREIGN PATENT DOCUMENTS

| JP | A-07-268387 | 10/1995 |
| JP | A-10-152421 | 6/1998 |
| JP | A-11-139957 | 5/1999 |
| JP | A-2001-158735 | 6/2001 |
| JP | A-2001-158736 | 6/2001 |
| JP | A-2001-192315 | 7/2001 |
| JP | A-2007-119361 | 5/2007 |
| JP | A-2008-105975 | 5/2008 |
| WO | WO 92/21323 | 12/1992 |

OTHER PUBLICATIONS

Darroch, P.I., Dagan, A., Granot, T., He, X., Gatt, S., Schuchman, H. Journal of Lipid Research 2005, 46, 2315-2324.*
Yarosh et al. Horm Res 2000, 54 (5-6), 318-321.*
Rawlings et al. Journal of Investigative Dermatology 1993, 103, 731-740.*
Iida, T. Fragrance Journal 2004, 32 (3), 41-47, Abstract.*
International Search Report for PCT/JP2009/003605, I.A. fd: Jul. 30, 2009, mailed Sep. 29, 2009 from Japanese Patent Office, Tokyo, Japan.
International Preliminary Report on Patentability, Chapter I of the Patent Cooperation Treaty, including the Written Opinion for PCT/JP2009/00365, I.A. fd: Jul. 30, 2009, issued Mar. 8, 2011 from the International Bureau of WIPO, Geneva, Switzerland.
Masaki, H., "Lysophosphatidic acid is an effective agent for epidermal care," Fragrance J 37:31-34 (May 2009), Tokyo, Japan.
Tanaka, S., "Cyclic phosphatidic acid (cPA)—A control of the skin moisture content by the lipid mediator" (ISR Title: "Lipid mediator for controlling water content of the skin"), Fragrance J 37:97-102 (Apr. 2009), Tokyo, Japan.
Modrak, D.E., et al., "Sphingolipid targets in cancer therapy," Mol. Cancer Ther 5:200-208 (Feb. 2006), Am. Assoc. for Cancer Research, Philadelphia, PA.
"Notification of the First Office Action," for Chinese patent application No. CN 200980120555.7, mailed Dec. 20, 2012, Patent Office of the People's Republic of China, Beijing, China.

* cited by examiner

*Primary Examiner* — Sreeni Padmanabhan
*Assistant Examiner* — Irina Neagu
(74) *Attorney, Agent, or Firm* — Sterne, Kessler, Goldstein & Fox P.L.L.C.

(57) ABSTRACT

Provided are a drug, a cosmetic, etc. for promoting production of ceramide.
Provided is a ceramide production promoter including a compound represented by the formula (1) or salts thereof as an active ingredient (in the formula, $R^1$ represents a phosphono group or a hydrogen atom, $R^2$ represents an alkyl group having 8 to 24 carbon atoms or an acyl group having 8 to 24 carbon atoms, and $R^3$ represents an alkyl group having 1 to 24 carbon atoms when $R^1$ represents a phosphono group or represents a phosphono group when $R^1$ represents a hydrogen atom, or a salt thereof as an active ingredient.

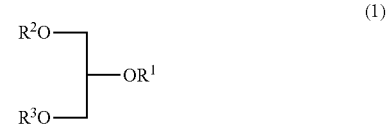

(1)

8 Claims, 1 Drawing Sheet

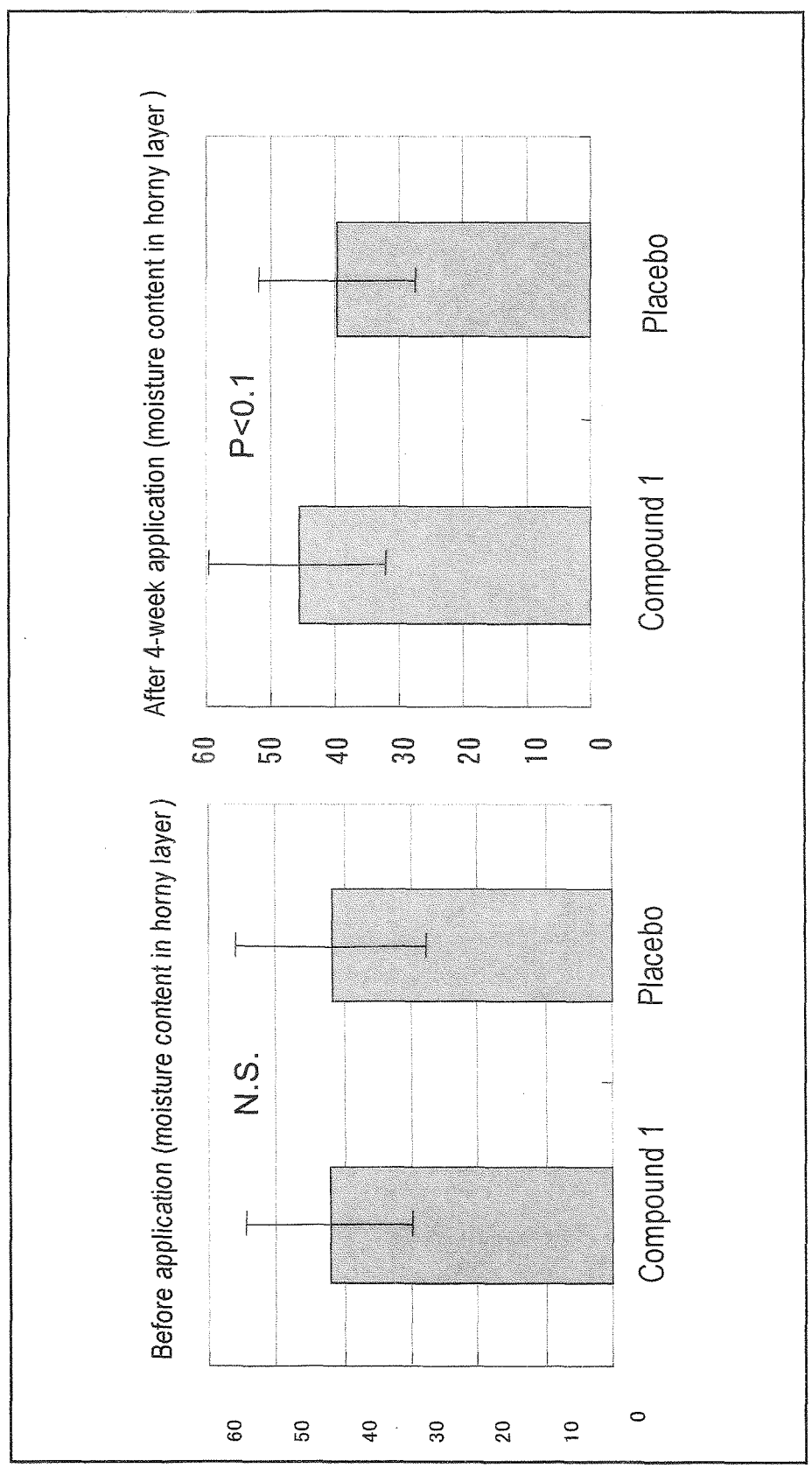

CERAMIDE PRODUCTION PROMOTER

FIELD OF THE INVENTION

The present invention relates to a ceramide production promoter for increasing ceramide.

BACKGROUND OF THE INVENTION

Ceramide, which is one of sphingolipids, is a lipid that presents in an entire living body in a minute amount, but accounts for more than half of the lipids in the horny layer, which is an outermost layer of the skin, and the ceramide plays an important role in the moisturizing mechanism and barrier mechanism of the skin. The ceramide is known to exert its moisturizing function through the formation of a lamella structure after being produced in epidermal cells and secreted in between corneocytes.

However, many reports indicate that, in the case of a skin disease such as dry skin, rough skin, atopic dermatitis, senile xerosis, or psoriasis, healthy metabolism of ceramide is inhibited, to thereby lower the amount of ceramide in lipids between corneocytes, resulting in, for example, deteriorating the moisturizing function or barrier function of the skin.

For such skin diseases, attempts have been made as methods of supplementing the decreased ceramide from outside, but there is such a problem that along-term effect cannot be obtained.

Further, in recent years, it has been reported that phenomena such as apoptosis, differentiation induction, and proliferation inhibition are induced by enhancing production of intercellular ceramide, and thus the ceramide has attracted attention as an intercellular signal molecule for controlling cell proliferation, differentiation, apoptosis or the like. For example, it is known that addition of C2-ceramide (D-erythro-N-acetylsphingosine), which is a ceramide analogue, from the outside of cells induces phenomena such as apoptosis, differentiation induction, and proliferation suppression, or a treatment of cells with bacterial sphingomyelinase causes accumulation of ceramide due to degradation of sphingomyelin to thereby induce inhibition of cell proliferation and apoptosis as in the case of addition of C2-ceramide.

Therefore, it is considered that a substance which promotes production of ceramide is expected to have effects such as proliferation inhibition, differentiation induction, and apoptosis induction of animal cells, and furthermore is expected to have therapeutic effects on diseases due to cell proliferation or abnormal differentiation, such as inflammatory diseases and malignant tumors (Non Patent Document 1).

Moreover, it has been reported that the ceramide has an effect of inhibiting bone resorption, an effect of strengthening bone, and an effect of inhibiting decrease in alveolar bone, and is useful for preventing and ameliorating bone and joint diseases such as osteoporosis, bone fracture, low back pain, and rheumatism (Patent Document 1), and has an effect of preventing periodontal diseases (Patent Document 2). Therefore, a ceramide production-promoting substance is expected to exert therapeutic effects on such diseases.

Moreover, it has been reported that the ceramide has an effect of imparting firmness or hardness to the hair and an effect of improving the feel of the hair (Patent Document 3), and the ceramide production-promoting substance may be expected to exert such effects.

On the other hand, 1,3-dialkylglyceryl 2-phosphate, which is phosphorylated glyceryl ether, or a salt thereof is known to have a skin-washing effect (Patent Document 4). However, it has not been known that 1,3-dialkylglyceryl 2-phosphate or a salt thereof have a ceramide production-promoting effect and a moisturizing effect.

Moreover, a phosphorylated glyceryl ether derivative such as a salt of 1-alkylglycerol-3-phosphate is known to have an effect of improving elasticity of the skin and an effect of tightening up the skin (Patent Document 5) and has been reported to be used as a bath agent (Patent Document 6), etc. However, it has been completely unknown that the phosphorylated glyceryl ether derivative has an effect of promoting production of ceramide.

PRIOR ART DOCUMENTS

Patent Document
  Patent Document 1: JP-A-2001-158736
  Patent Document 2: JP-A-2001-158735
  Patent Document 3: JP-A-10-152421
  Patent Document 4: JP-A-07-268387
  Patent Document 5: JP-A-2001-192315
  Patent Document 6: JP-A-11-139957
Non Patent Document
  Non Patent Document 1: Molecular Cancer Therapeutics, 5(2), 200-8 (2006).

SUMMARY OF THE INVENTION

1) The present invention relates to a ceramide production promoter, including a compound represented by the following formula (1):

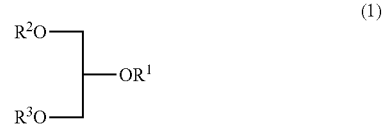

(1)

(wherein $R^1$ represents a phosphono group or a hydrogen atom, $R^2$ represents an alkyl group having 8 to 24 carbon atoms or an acyl group having 8 to 24 carbon atoms, and $R^3$ represents an alkyl group having 1 to 24 carbon atoms when $R^1$ represents a phosphono group or represents a phosphono group when $R^1$ represents a hydrogen atom) or a salt thereof as an active ingredient.

2) Further, the present invention relates to a moisturizing agent, including a compound represented by the above formula (1):

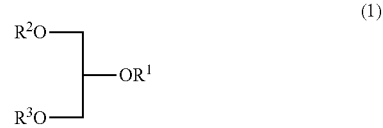

(1)

(wherein $R^1$ represents a phosphono group, $R^2$ represents an alkyl group having 8 to 24 carbon atoms, and $R^3$ represents an alkyl group having 1 to 24 carbon atoms) or a salt thereof as an active ingredient.

3) Further, the present invention relates to use of a compound represented by the formula (1) for producing the ceramide production promoter according to the above item (1).

4) Further, the present invention relates to use of a compound represented by the formula (1) for producing the moisturizing agent according to the above item (2).

5) Further, the present invention relates to a method of promoting ceramide production, including administering a compound represented by the following formula (1):

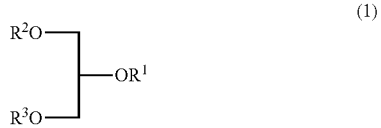

(wherein $R^1$ represents a phosphono group, $R^2$ represents an alkyl group having 8 to 24 carbon atoms, and $R^3$ represents an alkyl group having 1 to 24 carbon atoms) or a salt thereof to a person who wants to moisturize his or her skin.

BRIEF DESCRIPTION OF THE DRAWING

FIG. 1 A diagram illustrating the moisture contents in the horny layer after application of a 1% Compound 1-containing sample.

EMBODIMENT FOR CARRYING OUT THE INVENTION

The present invention relates to providing a drug, cosmetic, etc. for promoting production of ceramide.

The inventors of the present invention have searched for a highly safe compound and, surprisingly, have found that a specific phospholipid derivative has a ceramide production promoting effect and can be used as a ceramide production promoter.

A ceramide production promoter of the present invention increases ceramide and is useful as a drug, etc. for preventing or ameliorating inflammatory diseases, bone and joint diseases, periodontal diseases, etc., or as a cosmetic, etc. for imparting firmness or hardness to the hair and improving the feel of the hair.

Moreover, the ceramide production promoter of the present invention increases ceramide in lipids between corneocytes and is useful as a cosmetic, drug, etc. for recovering or maintaining the barrier function and moisturizing function of the skin.

In the formula (1), $R^2$ may be any of a linear or branched alkyl group having 8 to 24 carbon atoms, preferably 10 to 22 carbon atoms, and more preferably 12 to 20 carbon atoms.

Examples of the above-mentioned alkyl group having 8 to 24 carbon atoms include octyl, nonyl, decyl, undecyl, dodecyl, tridecyl, tetradecyl, pentadecyl, hexadecyl, heptadecyl, octadecyl, nonadecyl, icosyl, docosyl, tricosyl, tetracosyl, 2-heptylundecyl, isostearyl, 12-methylheptadecyl, 2-octyldodecyl, 3,7-dimethyloctyl, 3,7-dimethyloctan-3-yl, a 2-hexyldecyl, 3,7,11-trimethyldodecyl, 1,1,3,3-tetramethylbutyl, 3,7,11,15-tetramethylhexadecyl, 3,5,5-trimethylhexyl, 2,3,4-trimethylpentan-3-yl, and 2,3,4,6,6-pentamethylheptan-3-yl.

Further, when $R^1$ represents a phosphono group, $R^2$ represents preferably an alkyl group having 8 to 24 carbon atoms. Of the above-mentioned alkyl groups each having 8 to 24 carbon atoms, preferred examples include n-tetradecyl, n-hexadecyl, n-octadecyl, and isostearyl. Of those, n-tetradecyl is more preferred.

On the other hand, when $R^1$ represents a hydrogen atom, of the above-mentioned alkyl groups each having 8 to 24 carbon atoms, preferred examples thereof in $R^2$ include n-dodecyl, n-tetradecyl, n-octadecyl, i-octadecyl, 2-heptylundecyl, isostearyl, 12-methylheptadecyl, and 2-octyldodecyl. Of those, n-dodecyl, n-tetradecyl, n-octadecyl, 2-heptylundecyl, isostearyl, 12-methylheptadecyl, 2-octyldodecyl, and hexadecyl are more preferred.

Further, in $R^2$, the acyl group having 8 to 24 carbon atoms is preferably an alkylcarbonyl group having 8 to 24 carbon atoms, and more preferably an alkylcarbonyl group having 10 to 22 carbon atoms. Preferred examples thereof include decanoyl, lauroyl, myristoyl, palmitoyl, and stearoyl. Of those, palmitoyl is more preferred.

Further, $R^3$ represents preferably an alkyl group having 1 to 24 carbon atoms and may be any of a linear or branched alkyl group having 1 to 24 carbon atoms, preferably 1 to 10 and more preferably 1 to 6 carbon atoms.

In $R^3$, preferred examples of the alkyl group having 1 to 24 carbon atoms include methyl, ethyl, n-propyl, i-propyl, n-butyl, i-butyl, tert-butyl, pentyl, neopentyl, hexyl, heptyl, octyl, nonyl, decyl, undecyl, dodecyl, tridecyl, tetradecyl, pentadecyl, hexadecyl, heptadecyl, octadecyl, nonadecyl, icosyl, docosyl, tricosyl, tetracosyl, 2-heptylundecyl, isostearyl, 12-methylheptadecyl, 2-octyldodecyl, 3,7-dimethyloctyl, 3,7-dimethyloctan-3-yl, 2-hexyldecyl, 3,7,11-trimethyldodecyl, 1,1,3,3-tetramethylbutyl, 3,7,11,15-tetramethylhexadecyl, 3,5,5-trimethylhexyl, 1-isopropyl-1,2-dimethylpropyl, and 1-isopropyl-1,2,4,4-tetramethylpentyl. Of those, methyl, ethyl, n-propyl, i-propyl, n-butyl, i-butyl, and tert-butyl are preferred, and an ethyl group is more preferred.

In addition, in the present invention, the salt of the compound represented by the formula (1) may be any pharmaceutically acceptable salt. Examples of the salt include: alkali metal salts such as a lithium salt, a sodium salt, and a potassium salt; alkaline-earth metal salts such as a calcium salt and a magnesium salt; alkylamine salts such as a trimethylamine salt and a triethylamine salt; ammonium salts such as a quaternary ammonium salt; alkanolamine salts such as a triethanolamine salt, a diethanolamine salt, and a monoethanolamine salt; and basic amino acid salts such as a lysine salt, a histidine salt, and an arginine salt. Of those, a sodium salt, a potassium salt, and an arginine salt are preferred, and an arginine salt is more preferred.

As mentioned above, the compound of the present invention includes a compound represented by the following formula (1-a):

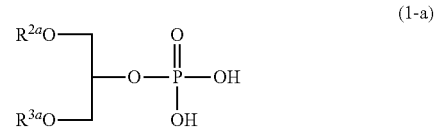

(wherein $R^{2a}$ represents an alkyl group having 8 to 24 carbon atoms, and $R^{3a}$ represents an alkyl group having 1 to 24 carbon atoms) and a compound represented by the following formula (1-b):

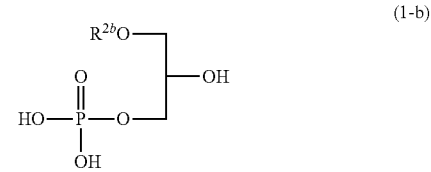

(wherein $R^{2b}$ represents an alkyl group having 8 to 24 carbon atoms or an acyl group having 8 to 24 carbon atoms), and the compound represented by the formula (1-a) is preferred.

The compound represented by the formula (1) in the present invention or a salt thereof may be produced by a known method (for example, JP-A-2002-187817) or may be obtained by extracting naturally-derived one.

For example, the compound may be obtained by phosphorylating 1,3-dialkylglycerol and, if desired, appropriately neutralizing the resultant product with an alkali which forms the above-mentioned salts.

As a phosphorylation reagent, for example, phosphorus oxychloride, phosphorus trichloride, phosphorus pentachloride, polyphosphoric acid, water and phosphoric anhydride, phosphoric acid and phosphoric anhydride, etc. may be used (Lecture of Experimental Chemistry (Jikken Kagaku Kouza) 1, Organic compound synthesis I, p 206-210, Kagaku-Dojin Publishing Co., Inc.). The resultant compound may be appropriately subjected to separation and purification by known methods. Note that 1,3-dialkylglycerol is a known compound, and its raw material, i.e., an alkyl glycidyl ether may be produced by a known method (JP-A-56-63974) and may be obtained by, for example, a reaction between the alkyl glycidyl ether and an alcohol in the presence of an appropriate acid or base.

As shown in Examples described below, the compound represented by the formula (1) of the present invention or the salts thereof have an effect of increasing the amount of ceramide in normal human keratinocytes. Ceramide plays an important role in the moisturizing mechanism and barrier mechanism of the skin (IMOKAWA Genji: Journal of Japanese Cosmetic Science Society, 1(4), 250-253, 1991). In this description, the moisturizing function means an action of providing skin with suppleness and making the skin smooth and beautiful due to the skin with adequate amount of moisture, and the barrier function means not only an action of preventing loss of water in the body and avoiding the body from drying but also an action of preventing a foreign substance from invading the body from the outside.

Therefore, the compound represented by the formula (1) or (1-a) of the present invention or a salt thereof can be used as a ceramide production promoter or a moisturizing agent or can be used for producing a ceramide production promoter or a moisturizing agent. The ceramide production promoter or moisturizing agent can be used as a drug, quasi drug, cosmetic, etc. for increasing ceramide in the horny layer to recover or maintain the barrier function and moisturizing function of the skin. Further, the concept of the ceramide production promoter or moisturizing agent can be ceramide production promotion or moisture retention, and the promoter or agent may be used as a quasi drug or cosmetic which indicates the concept, if required.

The ceramide production promoter of the present invention is useful as a cosmetic, drug, etc. for increasing ceramide in the horny layer to recover or maintain the barrier function and moisturizing function of the skin.

The compound represented by the formula (1), which has the ceramide production-promoting effect, is expected to have effects such as proliferation inhibition, differentiation induction, and apoptosis induction of animal cells. Accordingly, the compound can be used as a drug, quasi drug, etc. for preventing or treating diseases due to cell proliferation or abnormal differentiation such as inflammatory diseases and malignant tumors (the above-mentioned Non Patent Document 1) or can be used as a drug, quasi drug, etc. for preventing or ameliorating bone and joint diseases such as osteoporosis, bone fracture, low back pain, and rheumatism or periodontal diseases (the above-mentioned Patent Document 1 and 2). Moreover, the compound can be used as a quasi drug or cosmetic for imparting firmness or hardness to the hair and for improving the feel of the hair (the above-mentioned Patent Document 3). The concept of the ceramide production promoter can be ceramide production promotion, and the promoter may be used as a quasi drug or cosmetic which indicates the concept, if required.

In the case where the ceramide production promoter and moisturizing agent of the present invention are used as drugs, the administration form may be any of oral administration using, for example, tablets, capsules, granules, powders, or syrups, or parenteral administration using injections, external preparations such as ointments or creams, suppositories, or percutaneous absorbers. In order to prepare such medicinal preparations, the compound represented by the formula (1) of the present invention or the salts thereof may be used singly or inappropriate combination with other pharmacologically acceptable excipients, binders, fillers, disintegrants, surfactants, lubricants, dispersants, buffers, preservatives, flavoring agents, perfumes, coating agents, carriers, diluents, etc.

The content of the compound represented by the formula (1) of the present invention or the salts thereof in each of the preparations is preferably 0.001 to 20 mass % and more preferably 0.01 to 5 mass %.

Further, in the case where the ceramide production promoter and moisturizing agent of the present invention are used as drugs, the daily dose per adult is, for example, 0.1 to 2000 mg, and preferably 1 to 500 mg in terms of the compound represented by the formula (1) in the present invention or a salt thereof.

Further, in the case where the ceramide production promoter and moisturizing agent of the present invention are used as quasi drugs or cosmetics, the promoter and agent may be formed into external preparations for skin, cleansing agents, or make up cosmetics, and depending on usage, may be supplied in a variety of dosage forms such as beauty essences, skin toners, massage agents, lotions, milky lotions, gels, creams, ointments, powders, packs, granules, foundations, lipsticks, bath additives, shampoos, hair conditioners, hair tonics, tablets, capsules, absorbent articles, or sheet-shaped products. Such quasi drugs and cosmetics having a variety of dosage forms may be prepared using only the compound represented by the formula (1) of the present invention or a salt thereof, or using the compound or a salt thereof in appropriate combination with oily components, moisturizing agents, powders, pigments, emulsifiers, solubilizers, cleansing agents, ultraviolet absorbers, thickeners, medicinal components, perfumes, resins, antibacterial and antifungal agents, botanical extracts, alcohols, etc., which may be blended in quasi drugs, skin cosmetics, and cleansing agents. Note that the medicinal component may include other moisturizing components such as sodium hyaluronate.

The content of the compound represented by the formula (1) of the present invention or a salt thereof in the quasi drug or cosmetic is 0.001 to 20 mass %, and more preferably 0.1 to 5 mass %.

EXAMPLES

Production Example 1

Production of
1-n-tetradecyl-3-ethylglycerol-2-phosphate arginine salt (Compound 1)

Under nitrogen stream, 30 g of sodium ethoxide was added to 851.8 g (18.5 mol) of ethanol, and the mixture was heated to 80° C. Then, 500 g (1.85 mol) of tetradecyl glycidyl ether were added dropwise thereto. The mixture was stirred for 18 hours at the same temperature. Thereafter, ethanol was distilled off, and 10.8 g of 85% phosphoric acid was added thereto, followed by washing the resultant mixture with water three times. After water washing, distillation was performed under reduced pressure, to thereby obtain 446 g of 1-tetradecyl-3-ethylglycerol (yield 76.2%).

232 g (1.51 mol) of phosphorus oxychloride were dissolved in 200 ml of toluene, and the mixture was cooled to 10° C. or less under nitrogen atmosphere. Then, a mixed solution of 400.0 g (1.26 mol) of the obtained 1-tetradecyl-3-ethylglycerol and 400 ml of toluene was added dropwise thereto, and further, a mixed solution of 140.6 g (1.39 mol) of triethylamine and 100 ml of toluene was added dropwise thereto over 30 minutes. The mixture was stirred for 4 hours at the same temperature, and then 800 g of water were gradually added, followed by stirring at 50° C. for 1 hour. Toluene and isopropyl alcohol were added, and the aqueous layer was separated. After that, the upper layer was washed, and the solvent was distilled off, to thereby obtain 511 g of a clear and colorless oily product. 200 g of the product was dissolved in an ethanol-hexane mixed solvent, and 86.5 g (0.496 mol) of L-arginine was added thereto, followed by stirring at 60° C. until the mixture became homogeneous. The mixture was then cooled and charged in acetone, and precipitated crystals were filtrated. After that, the resultant was dried under reduced pressure, to thereby obtain 266 g of 1-n-tetradecyl-3-ethylglycerol-2-phosphate arginine salt (yield 94%).

IR ($cm^{-1}$, ATR method): 3159, 2922, 2853, 1632, 1110, 1053, 919

$^1$H-NMR ($D_2O$, ppm): 0.67-1.73 (m, 32H), 3.03 (t, J=6 Hz, 2H), 3.28-3.59 (m, 11H), 4.11 (m, 1H)

Production Example 2

Production of
1-isostearyl-3-butylglycerol-2-phosphate sodium salt (Compound 2)

2.10 g (13.7 mmol) of phosphorus oxychloride was dissolved in 10 ml of tetrahydrofuran, and the mixture was cooled to 10° C. or less under nitrogen atmosphere. Thereafter, a mixed solution of 5.00 g (12.5 mmol) of 1-isostearyl-3-butylglycerol and 10 ml of tetrahydrofuran was added dropwise, and further, a mixed solution of 1.26 g (12.5 mmol) of triethylamine and 10 ml of tetrahydrofuran was added dropwise over 30 minutes. The mixture was stirred for 2 hours at the same temperature, and then 1 g of water was added thereto, followed by stirring at 50° C. for 5 hours. Diethyl ether was added thereto, and the aqueous layer was separated. After that, the upper layer was washed, and the solvent was distilled off, to thereby obtain 6.18 g of a clear and colorless oily product. A solution obtained by dissolving 1.05 g of sodium hydrogen carbonate in 50 g of water was added thereto, and the mixture was stirred at 50° C. until the mixture became homogeneous, followed by cooling. Diethyl ether was added thereto, and the aqueous layer was separated, followed by drying under reduced pressure, to thereby obtain 3.49 g of 1-isostearyl-3-butylglycerol-2-phosphate sodium salt (yield 55.5%). Note that 1-isostearyl-3-butylglycerol was synthesized using 1-isostearylglycidyl ether and butanol in the same way as in Production Example 1.

IR ($cm^{-1}$, ATR method): 2956, 2923, 2854, 1653, 1464, 1377, 1105, 985

$^1$H-NMR ($D_2O$, ppm): 0.65-1.73 (m, 42H), 3.02 (t, J=6 Hz, 2H), 3.28-3.59 (m, 11H), 4.10 (m, 1H)

Test Example 1

Ceramide Production Promotion Test

<Culture Condition>

Normal human epidermal keratinocytes (NHEK(F)) were seeded into an EpiLife-KG2 (KURABO INDUSTRIES LTD.) 6-well Plate and cultured until the cells became confluent. Thereafter, in replacement of EpiLife-KG2 (containing no proliferation addition factor), Compound 1 (5 mM) and Compound 2 (1 mM) prepared in Production Examples or a control solution (10% ethanol) was added thereto in an amount of 1%. Culture was performed for 3 days, and the cells in each well were separately collected.

<Lipid Extraction>

Lipids were extracted from the collected cells by Bligh and Dyer method. The extracts were dried with nitrogen, and the residues were redissolved in chloroform and methanol, to thereby prepare lipid samples. Note that the amounts of proteins were determined by a BCA method.

<Analysis of Ceramide Amount>

The extracted lipids were subjected to horizontal development twice by using thin layer chromatography (TLC) and chloroform:methanol:acetic acid=190:9:1. The resultant was sprayed with a copper sulfate solution and heated on a hot plate, to thereby detect ceramide. Thereafter, the resultant values were divided by respective protein amounts to calculate amounts of ceramide. Table 1 shows the results. The numerical values shown in the table are relative values when the amount of ceramide in the control is defined as 1.

TABLE 1

| Test Compound | Amount of ceramide (relative value) |
|---|---|
| Compound 1 | 3.3 |
| Compound 2 | 1.5 |

Test Example 2

Test on Effect of Improving Moisture Content in Human Horny Layer

1 Test Contents 1.1 Test Subjects

Ten men (25 to 40-year-old: mean age 30.5)

1.2 Samples

A solution containing 1% Compound 1 and a placebo solution containing only a solvent were used as application samples. The solvent used was 95.0% ethanol:1,3-BG:purified water=20:10:70.

The samples were applied twice a day and five days a week. The amount of each sample per application was set to two drops (about 100 μl) from an eye drop bottle.

1.3 Test Method

The test was performed by applying the sample containing 1% Compound 1 to one side of the cheek and the placebo solution to the other side for 4 weeks, followed by measuring moisture contents in the horny layer using a Corneometer. The measurement was performed before the application and after the 4-week application at the same regions on the cheek, and the result of the 1% Compound 1-containing sample side was compared with that of the placebo side.

2. Results

FIG. 1 illustrates the results.

In the group in which the 1% Compound 1-containing sample was applied, the moisture content in the horny layer after the 4-week application of the sample was found to increase compared with that of the placebo-applied side (P<0.1: t-test both sides).

Production Example 3

(1) 1-Dodecylglycerol-3-phosphate disodium salt (Compound 3)

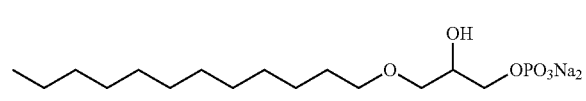

0.5 g (1.8 mmol) of dodecyl glyceryl ether was dissolved in hexane, and 0.85 g (9 mmol) of 105% polyphosphoric acid was added thereto at 50° C., followed by stirring at 70° C. for 12 hours. Thereafter, 10 g of distilled water was added thereto, and the mixture was further stirred for 3 hours and allowed to stand to cool. After that, ethanol was added thereto, and the aqueous layer was separated. The organic layer was concentrated, and then, purified water and sodium hydroxide were added thereto, followed by freeze-drying, to thereby obtain 0.66 g of 1-dodecylglycerol-3-phosphate disodium salt.

After that, Compounds 4 to 9 were each synthesized by the same method as that in (1).

(2) 1-Tetradecylglycerol-3-phosphate monoarginine salt (Compound 4)

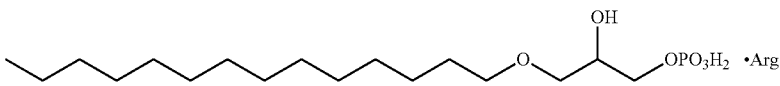

(3) 1-Octadecylglycerol-3-phosphate disodium salt (Compound 5)

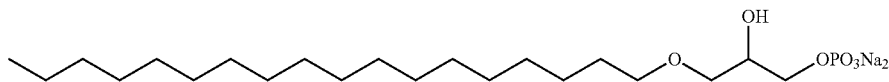

(4) 1-(2-Heptylundecyl)glycerol-3-phosphate monoarginine salt (Compound 6)

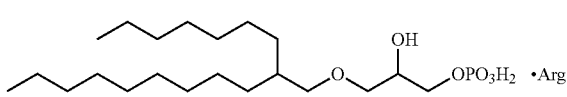

(5) 1-Isostearylglycerol-3-phosphate monoarginine salt (Compound 7)

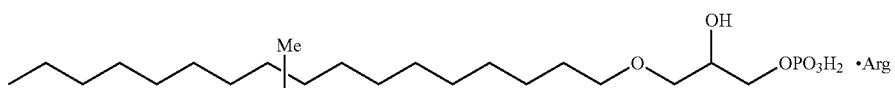

(6) 1-(12-Methylheptadecyl)glycerol-3-phosphate dipotassium salt (Compound 8)

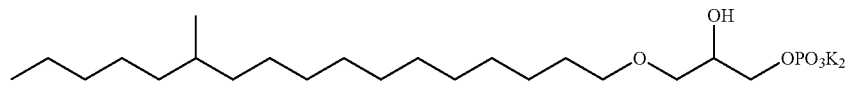

(7) 1-(2-Octyldodecyl)glycerol-3-phosphate monoarginine salt (Compound 9)

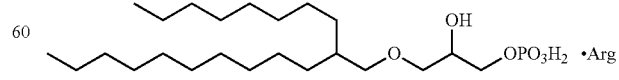

In addition, Compound 10 and Comparative Compound 1 shown below were purchased, and used in the following test.

(8) 1-Palmitoyl-sn-glycerol-3-phosphate sodium salt (Compound 10)

The compound used was purchased from Alexis Biochemicals Ltd.

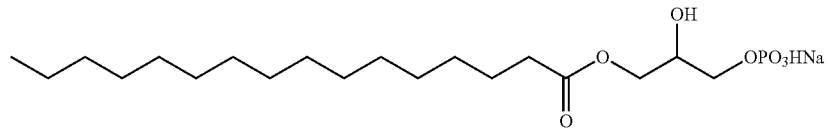

Comparative Compound 1: monoalkyl (having an average alkyl chain length of C13) phosphate potassium salt (Kao Corporation)

Test Example 3

Ceramide Production Promotion Test

<Culture Condition>

Normal human epidermal keratinocytes (NHEK(F)) were seeded into an EpiLife-KG2 (KURABO INDUSTRIES LTD.) 6-well Plate and cultured until the cells became confluent. Thereafter, in placement of EpiLife-KG2 (containing no proliferation addition factor), respective solutions of Compounds 3 to 10 and Comparative Compound 1 described above (Compound 10: 1 mM, the other compounds: 5 mM) and control solutions (Compound 5 and Comparative Compound 1: 50% ethanol, Compound 10: 80% ethanol, the other compounds: 10% ethanol) were added thereto in an amount of 1%. Culture was performed for 3 days, and the cells in each well were separately collected.

<Lipid Extraction>

Lipids were extracted from the collected cells by a Bligh and Dyer method. The extracts were dried with nitrogen, and the residues were redissolved in chloroform and methanol, to thereby prepare lipid samples. Note that the amounts of proteins were determined by the BCA method.

<Analysis of Ceramide Amount>

The extracted lipids were subjected to horizontal development twice by using thin layer chromatography (TLC) and chloroform:methanol:acetic acid=190:9:1. The resultant were sprayed with a copper sulfate solution and heated on a hot plate, to thereby detect ceramide. Thereafter, the resultant values were divided by respective protein amounts to calculate amounts of ceramide. Table 2 shows the results. The numerical values shown in the table are relative values when the amount of ceramide in the control is defined as 1.

TABLE 2

| Test Compound | Amount of ceramide (relative value) |
|---|---|
| Compound 3 (10% Ethanol) | 3.1 |
| Compound 4 (10% Ethanol) | 4.3 |
| Compound 5 (50% Ethanol) | 2.6 |
| Compound 6 (10% Ethanol) | 4.0 |
| Compound 7 (10% Ethanol) | 18.9 |
| Compound 8 (10% Ethanol) | 10.4 |
| Compound 9 (10% Ethanol) | 4.1 |
| Compound 10 (80% Ethanol) | 1.7 |
| Comparative Compound 1 (50% Ethanol) | 0.6 |

As shown in Table 2, the compounds of the present invention were found to have effects of promoting production of ceramide in human keratinocytes.

What is claimed is:

1. A method of promoting ceramide production, comprising administering a compound represented by the following formula (1):

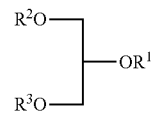

wherein $R^1$ represents a phosphono group, $R^2$ represents an alkyl group having 8 to 24 carbon atoms, and $R^3$ represents an alkyl group having 1 to 24 carbon atoms, or a salt thereof to a subject who wants to moisturize his or her skin and promoting said ceramide production in said subject as a result of said administering.

2. The method according to claim 1, wherein $R^3$ represents an alkyl group having 1 to 6 carbon atoms.

3. A method of promoting ceramide production, comprising administering a compound represented by the following formula (1):

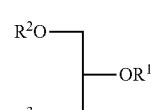

wherein $R^1$ represents a phosphono group or a hydrogen atom, $R^2$ represents an alkyl group having 8 to 24 carbon atoms or an acyl group having 8 to 24 carbon atoms, and $R^3$ represents an alkyl group having 1 to 24 carbon atoms when $R^1$ represents a phosphono group or represents a phosphono group when $R^1$ represents a hydrogen atom, or a salt thereof as an active ingredient, to a subject who wants to moisturize his or her skin, and promoting said ceramide production in said subject as a result of said administering.

4. The method of claim 3, wherein said $R^1$ is said hydrogen group.

5. The method of claim 4, wherein said $R^2$ is said alkyl group.

6. The method of claim 4, wherein said $R^2$ is said acyl group.

7. The method of claim 3, wherein said $R^1$ is said phosphono group and $R^2$ is said acyl group.

8. The method according to claim 7, wherein $R^3$ represents an alkyl group having 1 to 6 carbon atoms.

* * * * *